United States Patent
Chyba et al.

(10) Patent No.: US 8,306,780 B2
(45) Date of Patent: Nov. 6, 2012

(54) DATA QUALITY AND ANCILLARY DATA CHECKING FOR RAMAN SENSOR

(75) Inventors: Thomas H. Chyba, Tijeras, NM (US); Brian Kelly, Albuquerque, NM (US)

(73) Assignee: Exelis Inc., McLean, VA (US)

( * ) Notice: Subject to any disclaimer, the term of this patent is extended or adjusted under 35 U.S.C. 154(b) by 823 days.

(21) Appl. No.: 12/359,589

(22) Filed: Jan. 26, 2009

(65) Prior Publication Data

US 2010/0191506 A1 Jul. 29, 2010

(51) Int. Cl.
*G06F 11/30* (2006.01)
*G21C 17/00* (2006.01)

(52) U.S. Cl. ............................................. 702/182
(58) Field of Classification Search .................. 702/182
See application file for complete search history.

(56) References Cited

U.S. PATENT DOCUMENTS

| | | | |
|---|---|---|---|
| 6,608,677 | B1 | 8/2003 | Ray et al. |
| 7,254,501 | B1 * | 8/2007 | Brown et al. ............... 702/76 |
| 7,583,378 | B2 | 9/2009 | Rezac et al. |
| 2005/0162646 | A1 | 7/2005 | Tedesco et al. |
| 2007/0222981 | A1 | 9/2007 | Ponsardin et al. |
| 2008/0144012 | A1 | 6/2008 | Goetz et al. |
| 2009/0015829 | A1 * | 1/2009 | Rezac et al. ................ 356/301 |
| 2009/0237648 | A1 * | 9/2009 | Armstrong et al. ............ 356/72 |

FOREIGN PATENT DOCUMENTS

WO 2007101092 A2 9/2007

OTHER PUBLICATIONS

European Search Report, EP10150902, Mar. 9, 2011 (8 pages).
Ahura Scientific: "TruScan Antech Brochure", Jan. 1, 2007 (XP002619452), retrieved from the Internet: URL: http://www.antech.ie/media/file/Handheld/TruScan%20Antech%20Brochure.pdf (3 pages).
Ahura Scientific: "Ahura Truscan", Jan. 1, 2007 (XP002619453), retrieved from the Internet: URL:http://www.cmbcontrol.com.mx/pdf/ahura_truscan.pdf (3 pages).
Carter et al., "Standoff Detection of High Explosive Materials at 50 Meters in Ambient Light Conditions Using a Small Raman Instrument", vol. 59, No. 6, Mar. 17, 2005, pp. 769-775.

* cited by examiner

*Primary Examiner* — Michael Nghiem
(74) *Attorney, Agent, or Firm* — Edell, Shapiro & Finnan, LLC (57) ABSTRACT

Systems and methods for operating, particularly in the field, a Raman spectroscopy device that includes a laser, a spectrograph, an intensified charge coupled device (ICCD), and an autofocus subsystem. Before spectral data acquisition commences a series of ancillary data checks is performed to monitor operating conditions of at least the laser, the ICCD, and the autofocus subsystem. Further, after each Raman spectrum acquisition, a series of data quality checks is performed to enhance confidence in the just collected data. Only spectral data that passes the data quality checks are further processed. However, all spectral data are stored in a log file. When the log file reaches a predetermined capacity, the log file is closed, and a new round of ancillary data checks is performed to again monitor the status of the Raman spectroscopy device.

17 Claims, 4 Drawing Sheets

DATA QUALITY AND ANCILLARY DATA CHECKING FOR RAMAN SENSOR

FIELD OF THE INVENTION

Embodiments of the present invention relate to Raman spectrometry sensors, and more specifically to systems and methods for performing automated periodic evaluations of sensor equipment and collected spectral data.

BACKGROUND OF THE INVENTION

The danger of exposure to chemical or biological agents can be severe. Whether a result of unintended release by way of, e.g., an accident, or intentional delivery, it is desirable to quickly and accurately identify (1) the type of agent that has been released and (2) the precise area of contamination. Early and accurate detection of such dangerous substances can be a significant factor in reducing potential casualties and limiting further spreading of the agent, e.g., by wind, human and animal contact, etc.

In recent years, there has been an increased interest in developing and deploying nuclear, biological, and chemical (NBC) sensor technologies to quickly identify unknown substances, contaminants, and agents, even at very low concentrations. Some of these technologies are designed to measure surface-deposited contamination and use vehicles and associated test equipment to retrieve a physical sample of the contaminant and then employ extremely cumbersome and time-consuming processes based on a mechanical sampling wheel system to test for agents.

In view of the complexity of such approaches, newer, simpler, safer and more reliable technologies have been in demand. One emerging technology in response to this desire is referred to, generally, as "standoff surface detection," and refers to a category of technologies that permit detection of substances without actually having to physically come in contact with the substance of concern. The goal of these detection systems is to provide the capability to detect, identify, locate, quantify, warn, and report chemical or biological threats and thereby give military forces or civilian personnel sufficient early warning to avoid (further) contamination.

An example of a standoff surface detection system is a technology known as Laser Interrogation of Surface Agents (LISA) that has been developed by ITT (Wilmington, Del.). LISA uses a laser and associated sensor attached to a reconnaissance vehicle that looks for chemical agents on the ground (or any surface) using a technique known as Raman Scattering (or Raman Effect), which is an optical property that can be exploited to identify known chemical agents. Current ITT LISA systems have standoff ranges from 0.4 to 3 m and can provide detection on each single laser shot or pulse, at 25 pulses per second. This allows personnel manning the vehicle with the ability to perform on-the-move, real-time measurements of chemical agents on the ground. The LISA technology also provides detection teams the ability to create or generate a map with chemical agent contours that build up as detection is taking place.

Standoff biological agent detection is significantly more difficult than chemical detection. Specifically, it is difficult to discriminate and measure biological agents from naturally occurring background materials. Moreover, real-time detection and measurement of biological agents in the environment can be daunting because of the number of potential agents to be identified, the complex nature of the agents themselves, the countless number of similar microorganisms that are a constant presence in the environment, and the minute quantities of pathogen that can initiate infection. Potential biological agents can also disguise themselves in benign entities.

In light of these obstacles, approaches for detecting biological agents differ somewhat from those technologies that are employed to detect chemical agents. While the molecules that comprise biological agents are extremely complex and large in comparison to chemical agents, they are only made up of a very limited number of unique building blocks. As a result, it has been found that it is necessary to use a laser with very specific ultra-violet wavelengths to probe the biological agent in order to enhance its Raman signal.

In sum, whether for detection of chemical substances or biological substances, Raman spectroscopy is an evolving complex art and those skilled in the art appreciate that a Raman sensor along with its supporting equipment is a complex and sensitive apparatus even under the best of circumstances, such as under controlled laboratory conditions. Keeping such an apparatus operating properly in the field presents an even greater challenge. There is thus a need to provide improved Raman spectroscopy equipment and methods of operation thereof in order to effectively bring standoff surface detection to practical use, and particularly for extended field use.

SUMMARY OF THE INVENTION

Embodiments of the present invention provide systems and methods for operating, particularly in the field, a Raman spectroscopy device for stand off detection of chemical and biological agents. In an embodiment, the device includes a laser, a spectrograph, an intensified charge coupled device (ICCD), and an autofocus subsystem (including telescope collection optics), as well as a related processor and memory. In a preferred embodiment, before spectral data acquisition commences, a series of ancillary data checks (ADCs) is performed to monitor operating conditions (i.e., the health and status) of at least the laser, the ICCD, and the autofocus subsystem. Further, after each Raman spectrum acquisition, a series of data quality checks is performed to enhance confidence in the just collected data. Only spectral data that pass the data quality checks are further processed. However, all spectral data are preferably stored in a log file. When the log file reaches a predetermined capacity, the log file is closed, and a new round of ancillary data checks is performed to again monitor the status of the Raman spectroscopy device.

More specifically, in a preferred method in accordance with the present invention, after an initialization step of the apparatus, a series of ADCs is performed. These checks include, among other checks, monitoring of, for example, the ICCD's gain and array temperature, the laser's energy, gas pressure, and pulse count, and temperature, the device's overall temperature and humidity level, the autofocus' linear focus actuator status, and even general altitude and atmospheric data. These automated tests ensure that the health and status of the device is normal, thus providing confidence in the Raman spectral data to be acquired and to be processed in an effort to identify unknown chemical or biological agents.

If selected ones of the ADCs do not pass, the system may be placed back into a standby mode to prevent acquiring possible degraded or faulty data and to allow for possible servicing of the equipment. Other failed ADCs might result only in a warning to an operator of the system.

After completion of the first series of ADCs, the system acquires ten dark spectra, i.e., spectra without a corresponding laser pulse. A median of these ten spectra is then computed. This median represents current noise or background and is subtracted from subsequent laser induced spectra such that only the laser induced spectra is used for detection purposes.

Acquisition of laser induced Raman spectra is then initiated. After each collection of spectral data (preferably at a frequency of about 25 Hz), a series of data quality checks (DQCs) is performed including checking whether there has been problems with a linear focus actuator, whether the laser's energy was within a predetermined range, and whether the collected spectral data is saturated or has too low amplitude. In the latter two instances, a gain adjustment loop is initiated to adjust the gain of the ICCD to avoid saturation or low amplitude issues on subsequent spectral data collections.

When DQCs for a given Raman spectrum have all passed, that data may be designated along with other similarly qualified data for further processing, namely Raman spectrum pattern matching against a stored library of Raman spectra. All data (in the form of individual records), however, qualified or not, is preferably stored in a log file and the data records preferably include the results of the DQCs for respective data acquisitions. Once a log file is filled to a predetermined capacity (e.g., 3000 records), the log file is closed and stored and a new log file is opened. During this period, a second series of ADCs is performed, thereby again checking overall system status. Because the laser is pulsing at about 25 Hz, and the log file has a set capacity of about 3000 records, ancillary data checks are performed about once every two minutes, i.e., 3000 spectra/25 spectra per second=120 seconds. Accordingly, the Raman spectroscopy system is automatically and periodically being checked, thereby increasing confidence in the spectral data being collected and ensuring the system is in proper functioning order.

These and other features of the present invention, along with their attendant advantages, will be more fully appreciated upon a reading of the following detailed description in conjunction with the associated drawings.

DETAILED DESCRIPTION

For convenience, the list below defines acronyms used in the following detailed description.
ADC—Ancillary data check
CAPPS—Control, acquisition, processing, and power system
DQC—Data quality check
HV—High voltage
ICCD—Intensified Charged-Coupled Device
KS—Kinetic series
LFA—Linear focus actuator.
LPMT—Laser Power Module Temperature
MCPV—Micro-Channel Plate Voltage (representative of ICCD gain)

Generally, embodiments of the present invention provide an integrated Raman spectroscopy system, or simply "Raman sensor," with automated, periodic, data quality checks (DQCs) and ancillary data checks (ADCs) that provide feedback about, respectively, the nature and propriety of the Raman spectral data collected and the status of various subsystems and components of the Raman sensor. The DQCs and ADCs are preferably interposed at several different points in the course of Raman spectral data collection and processing to ensure that collected Raman spectra data is sufficiently reliable to process, and to further ensure that the Raman sensor, as a whole, is operating within nominal ranges, thereby providing increased confidence in the ultimate results of processed data and, in the end, confidence in an identification of an unknown substance or agent being analyzed.

Figure 1:
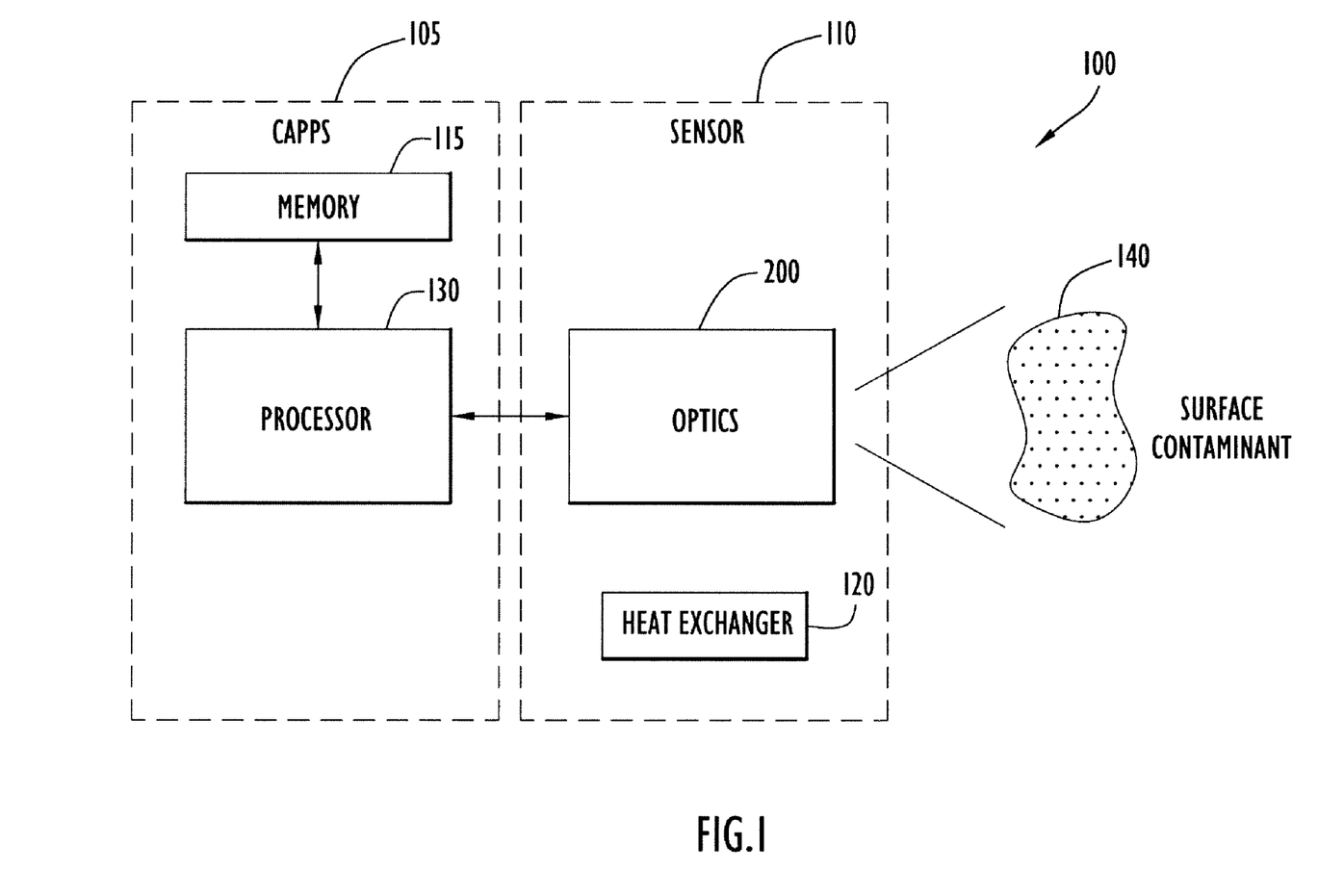
FIG. 1 is a diagram of a Raman spectroscopy system in accordance with an embodiment of the present invention.

With reference to FIG. 1, an overall Raman spectroscopy system 100 is depicted that includes a control, acquisition, processing and power system (CAPPS) 105 and a sensor 110. CAPPS 105 comprises, at a high level, memory 115, and processor 130. A power supply system is not shown. Sensor 110 comprises, at a high level, an optics module 200, which is described more fully below, and a heat exchanger module 120.

Memory 115 may comprise non-volatile read only memory (ROM) for storing processing instructions (discussed more fully later herein), global variables, initialization variables and routines, and a library of Raman signatures, among other things. Memory 115 may also comprise volatile random access memory (RAM) for storing the foregoing data, or other data (e.g., detected/collected Raman spectral data), sensor status readings, and user input/settings, among other things, including, alternatively, the data described as being stored in ROM. Memory 115 may still further comprise disk drives, flash memory, or any other suitable data storage technology.

Heat exchanger 120 is employed to heat or cool the sensor 110 and to maintain a steady temperature for the system and its components as analysis of collected spectral data can be detrimentally influenced by mechanical, electrical and optical components whose performance changes with high or drifting temperature. In an actual implementation, the CAPPS 105 is cooled only by fans internal to the CAPPS unit blowing through filters. The heat exchanger is needed because the sensor is preferably a sealed unit to protect it from external dirt and vapors (e.g. vehicle exhaust).

Processor 130 is a conventional processor suitable to run software routines for, among other things, providing overall system control, including management of inputs and outputs via a user interface (not shown), as well as control of and signals received from the various components of sensor 110. Processor 130 is preferably also capable of performing the requisite digital signal processing on collected spectral data and comparing the same to the library of Raman signatures stored in memory 115 to identify unknown substances. Processor 130 and memory 115 are in communication with one another, as shown, via conventional techniques, e.g., using a control/signal/data bus.

Optics module 200 (which is described in detail with reference to FIG. 2), is in communication with processor 130 and is arranged to irradiate, using a laser, an unknown substance, such as surface contaminant 140, collect resulting Raman spectral data, and pass the collected data to processor 130 for detailed analysis.

CAPPS 105 and sensor 110 are preferably encased in separate enclosures. The system 100 is further preferably configured to operate in the field, either as a jeep/truck mounted unit, or even as a man portable device. In either case, not only does the heat exchanger 120 need to compensate for heat generated internally to the sensor (such as by optics module 200), but the heat exchanger 120 must also compensate for a potentially wide range of ambient field conditions, ranging from, e.g., desert heat to winter ice and snow temperature conditions.

Figure 2:
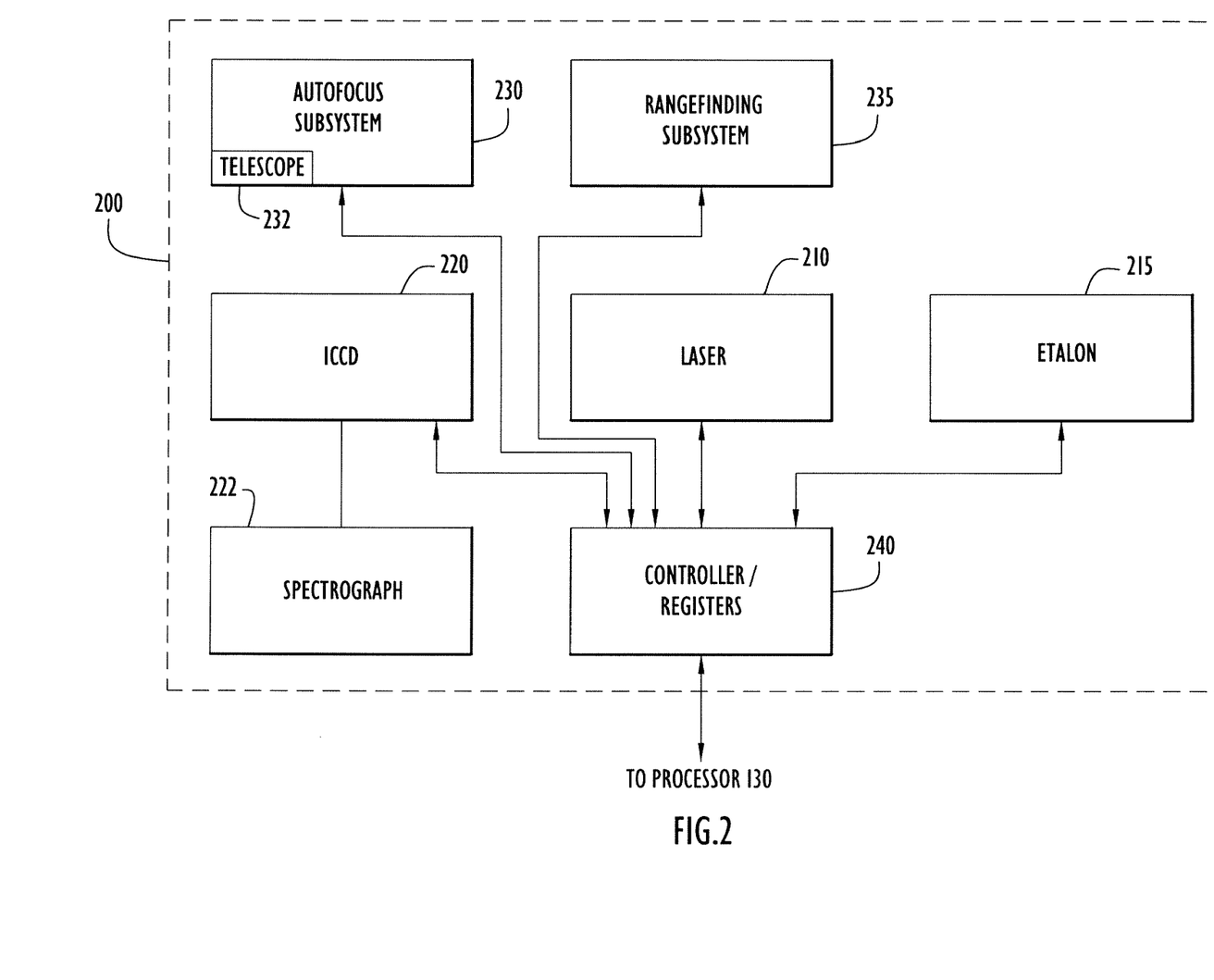
FIG. 2 depicts components of a Raman sensor module in accordance with an embodiment of the present invention.

With reference now to FIG. 2, optics module 200 of sensor 110 is more fully described.

At the heart of the optics module 200 is laser 210 that generates a coherent light beam. Laser 210 may produce a beam of light in the ultraviolet (UV) spectrum and be substantially monochromatic (i.e., a single wavelength or limited to a narrow range of wavelengths). An excimer or frequency-shifted Nd:YAG or Nd:YLF laser may be suitable for this purpose. Laser 210 preferably produces light energy resulting in returned optical energy that consists of enough Raman scattered optical energy (spectrum) to allow analysis using known spectroscopy techniques.

Associated with laser 210 is an etalon 215, which is used, as is well-known in the art, to increase the coherence length of the laser light. As will be described more fully later herein, selected operating parameters of both the laser 210 and etalon 215 are monitored in connection with ancillary data checks (ADCs) that are performed in connection with operating Raman system 100. It is noted that etalon 215 is only needed for specific lasers such as the excimer. Not all lasers would need it. There are a host of techniques to make a laser have a narrow linewidth. Even the excimer could be made spectrally narrow through other known methods.

Also included in optics module 200 is a spectrograph 222 and an intensified charge-coupled device (ICCD) 220 that serves as a pixilated detector. As is known in the art, the spectrograph 222 comprises a diffraction grating to disperse scattered radiation (resulting from laser irradiation) onto the ICCD 220. The ICCD 220 may be integrated with the spectrograph 222 as a single unit. A suitable ICCD that may be used in the instant system is model no. DK720A-25H-186 available from Andor Technology (Belfast, Northern Ireland).

Still with reference to FIG. 2, optics module 200 preferably also comprises an Autofocus subsystem 230 and Rangefinding subsystem 235. The ability to focus collection optics, such as a telescope 232, that passes light to the spectrograph/ICCD 222/220) allows for the collection of Raman spectra from safer distances, i.e., "standoff" distances. While the adjustment of the standoff distance is not required, the measurement precision is enhanced by providing this adjustability since the sensor has a limited depth of field for a given standoff range. Focusing may be accomplished by moving, via suitable actuators (motors, gears, etc.), e.g., an optical element of the telescope 232. Such systems are well known in the art. Focusing may also preferably be performed manually, although automated focusing is preferable.

Rangefinding subsystem 235 provides information regarding the range or distance of an object or unknown substance of interest. This information may be helpful for an Autofocus process in order to optimize the telescope focus and hence the amount of collected Raman light.

Controller/registers module 240 is preferably in electrical communication with each of the components in the optics module 200. Controller/registers module 240 may pass commands initiated from processor 130 to one or more components, and may further pass information from any one of the components back to processor 130. Controller/registers module 240 may also buffer information that is received from outputs of associated respective components, thereby realizing a more distributed overall system. Controller/registers module 240 may further be used, in accordance with embodiments of the present invention, to pass performance and status data regarding the several components so that such data can be used for data quality checks (DQCs) and ancillary data checks (ADCs) in the processor 130. Of course, controller/registers module 240 could be incorporated directly into processor 130 (in conjunction with memory 115) such that the several components of the optics module 200 are directly connected to the processor 130 without any intervening devices.

Figure 3:
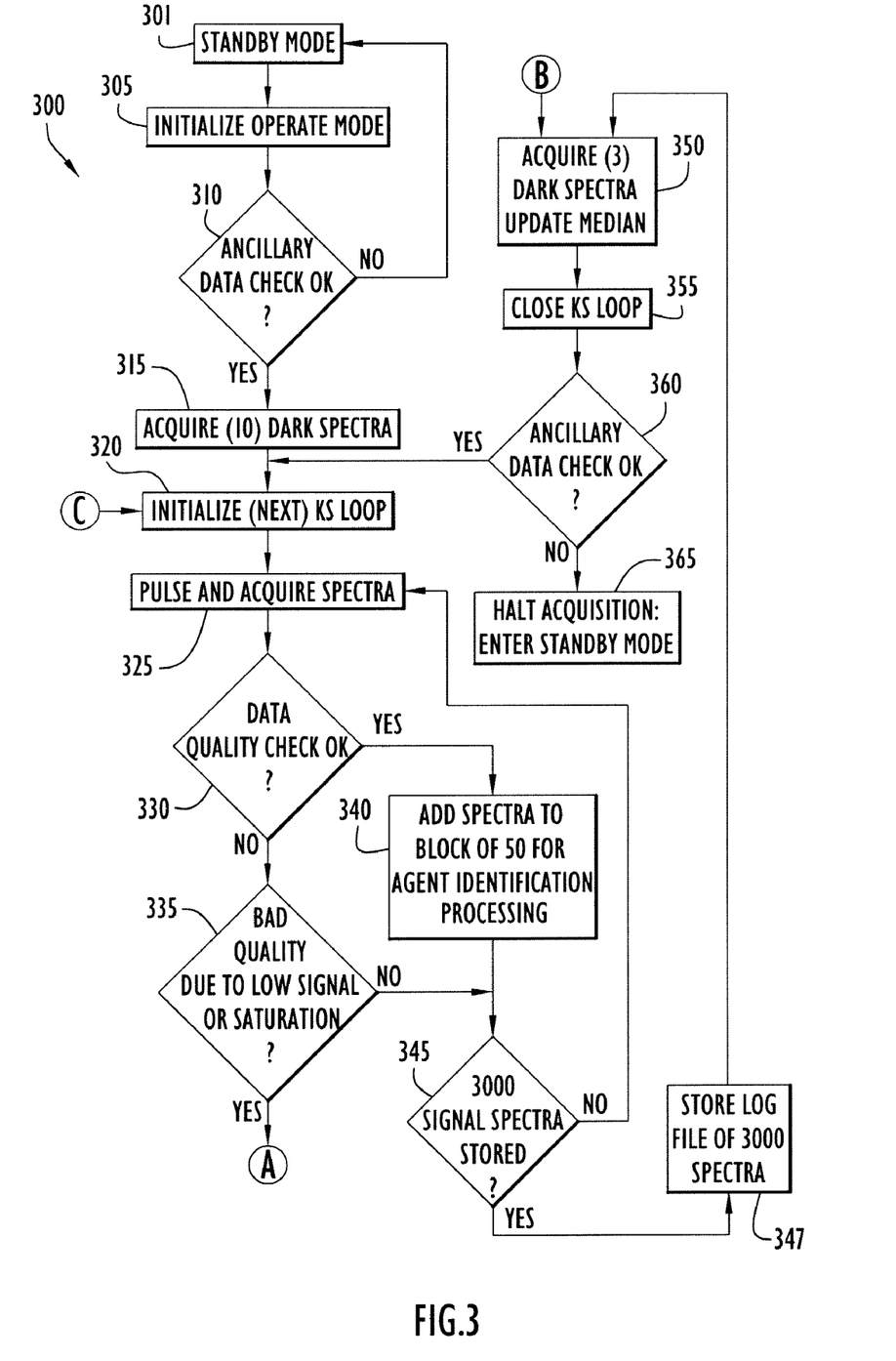
FIGS. 3 and 4 depict an exemplary series of steps for operating a Raman spectroscopy system in accordance with an embodiment of the present invention.

Reference is now made to FIG. 3 for a description of an exemplary series of steps 300 for operating the Raman sensor in accordance with an embodiment of the present invention. Step 301 represents a standby mode that is provided for when the system is first powered up, and after which the system may have completed a series of built-in-tests. For example, component temperatures, system health and status, ICCD noise levels, laser energy, and system calibration may be checked, among other things. The standby mode of step 301 is also a point in the sequence of process 300 at which messages may be presented to a user via a display or user interface (not shown). In essence, standby mode 301 is a system "idling" mode awaiting input from a user.

Once an indication is made that a user desires the system to move to an operational mode (e.g., via pushbutton, touch screen, etc.), sequence 300 proceeds to step 305, where the operate mode is initialized.

Once initialization step 305 is complete, sequence 300 moves to step 310 where a plurality of system checks are performed to determine the "health and status" of the overall Raman sensor 100. These system checks are formally referred to as ancillary data checks (ADCs). Preferred ADCs are categorized and described below.

Ancillary Data Checks (ADCs):

There are five (5) main categories of ADCs that are preferably routinely performed at predetermined points in sequence 300 in accordance with an embodiment of the present invention. These categories of ADCs pertain to: (A) ICCD checks, (B) Laser checks, (C) Sensor checks, (D) Autofocus checks, and (E) a miscellaneous checks. Each of these categories is described next.

(A) ICCD Checks:

It is desirable to know that ICCD 220 is operating properly so that data received from the device can be confidently relied upon. In this regard, at least some of the following checks are preferably made with respect to the ICCD 220.

(1) Verify ICCD high voltage (HV) is within tolerance of a predetermined setpoint. In this check, the ICCD's Micro-Channel Plate Voltage (MCPV) is checked three (3) times, 100 msec apart and a median is taken ("medianMCPVoltage"). A variable referred to as MCPGain is computed as follows:

MCPGain=200+ICCDHVSlope*(median MCPVoltage−ICCDHVat200).

Then, if |current gainsetting-mcpgain|> a set tolerance value, then the test is considered to have failed. This ICCD HV test confirms that the HV on the ICCD intensifier correctly corresponds to the current gain setting. In a preferred embodiment, a user display error need not be generated when the test fails, but an error may be written to a system log.

(2) Check ICCD temperature stability. This test calls a function in the ICCD to check if the ICCD array temperature is stable. If not, then the test fails. This test is particularly useful because a dark spectrum will shift or drift unless ICCD temperature is stable. Should the test fail, a warning is preferably provided to the user, but operation may still continue.

(3) Check ICCD array temperature. This is a straight test of the ICCD's current temperature. If the temperature is not within tolerance of the ICCDArrayTempSetPoint (a pre-determined value) then acquisition is preferably halted. The ICCD temperature may be in a run-away condition. The user is preferably warned to cool down the system.

(4) ICCDCaseTemperature. If the case temperature>limit1 (a predetermined value) then a warning is preferably provided to the user. If the case temperature>limit2 (another predetermined value) then acquisition is preferably halted, and the user is also warned to take corrective action.

(B) Laser Checks:

(1) LaserTotalPulseCount. If the total pulse count of the laser>limit1 (a predetermined value), then the user is notified that servicing will be needed in the near future. This check and ensuing warning precludes the laser from operating beyond its specified operating life, and is geared toward components that need replacement very infrequently, such as laser optical components (2) LaserPulseCountRefill. If>limit 1 (a predetermined value) then the user is preferably warned that a refill of the excimer laser gas will be needed after a specified number of mission hours. For non-gas lasers, this check could determine when other components that need regular or frequent replacement require maintenance, such as laser flashlamps or laser diodes.

(3) REX5HVSet. This is a setpoint for the laser high voltage. It directly relates to how much energy the laser produces. The laser has 2 modes: constant energy and constant voltage. In constant energy mode, the high voltage control is continually adjusted to maintain a predetermined laser energy. In constant voltage mode, the voltage is set to this value regardless of laser energy output. If the variable REX5HVSet>a predetermined value as received from the laser, the test fails, and the user is warned to refill the excimer laser gas at the next opportunity. However, spectral data acquisition need not be halted until a data quality check (described below) indicates that pulse energy is consistently too low. In a solid state laser, the high voltage at which flashlamps operate also increases up to a limit as the flashlamps age.

(4) REX5FilMon. This is a monitor for the laser filament (thyratron) voltage. The thyratron acts as a fast high voltage switch that triggers the laser action. It is one of the laser electronic components that has short lifetime (years). If the variable REX5FilMon is outside its allowable range (e.g., 6.0 or 7.0 volts) then this test fails, and the user is warned that thyratron needs replacing at the next opportunity.

(5) REX5GasPress. If REX5GasPress is outside of an allowable range (e.g., 3200 or 3900 Torr) then this test fails. Spectral data acquisition is halted and the user is informed that the gas pressure is out of range and that the laser must be refilled. This test accounts for other potential pressure problems such as a gas leak that causes the pressure to be too low.

(6) LaserTemp. If case temperature of the laser>limit1 (a predetermined value) then a warning is preferably provided to the user, and if>limit2 (another predetermined value) then data acquisition is preferably halted.

(7) EtalonTemp. If |etalon temperature-setpoint|>limit1 (a predetermined value) then the user is preferably warned, and if>limit2 (another predetermined value) then data acquisition is preferably halted.

(C) Sensor Checks:

(1) SensorTemp. If the internal ambient temperature of the sensor portion 110 of the system 100 is higher than a first limit, a warning may be given, and a temperature higher than a second limit will cause a halting of data acquisition or possibly a system shutdown.

SensorHumidity. If the humidity within the system is higher than a first limit, a warning may be given, and a humidity level temperature higher than a second limit will cause a data acquisition shut down.

(D) Autofocus Checks:

(1) LFAAmpTemp This test checks the case temperature of the amplifier that drives the electromagnetic motor of the linear focus actuator (LFA). If case temperature>limit1 (a predetermine value) then a warning is preferably provided, and if>limit2 (another predetermined value) then data acquisition is preferably halted and the LFA is temporarily powered down to cool.

(2) LFACompTemp. This test checks the Sensor Computer temperature. If the case temperature>limit1 (predetermine value) then a warning is preferably provided, and if>limit2 (another predetermined value) then data acquisition is preferably halted.

(3) LFABrakePosition. This test determines if the LFA's brake position is properly set. If not, data acquisition is halted and the auto focus system is reset.

(4) RangerOK. This check tests whether the communication between the Sensor Computer and the laser rangefinder is operating properly.

(5) PSDOK This test verifies that the telescope mirror position as determined by the position sensing device (PSD) lies within an allowable range. If results are not within an allowable range, then acquisition is halted.

(E) Miscellaneous Checks:

(1) AltitudeCal. This test combines information from a GPS receiver (not shown) with calibration information to confirm the current altitude, which can affect spectral calibration and thus data analysis. If the altitude has changed significantly since the last calibration, the user is prompted to perform a system recalibration.

(2) AtmosPress. Similarly, it may be desirable to confirm the current atmospheric pressure, as this metric may also influence spectral calibration and thus data analysis. If the atmospheric pressure has changed significantly since the last calibration, the user is prompted to perform a system recalibration.

(3) CAPPST. This test checks for CAPPS 105 temperature. A first and second limit may be implemented wherein the first limit generates a warning, while the second limit causes data acquisition to be halted or possibly force a system shutdown.

(4) SUHtExInT SUHtExInT is the Sensor Unit Heat Exchanger Inlet Temperature. This is, essentially, the ambient temperature of the vehicle cabin where the sensor resides. If the inlet temperature>limit1 then warn the user, if>limit2 then halt acquisition. Warn means advise user to take actions to cool the vehicle cabin. If acquisition is halted, then user action is required.

(5) SUHtExOutT SUHtExOutT is the Sensor Unit Heat Exchanger Outlet Temperature. This approximates the air temperature inside the sensor. If the outlet temperature>limit1 then warn the user, if>limit2 then halt acquisition. Warn means advise user to take actions to cool equipment. If acquisition is halted, then user action is required.

(6) LPMT LPMT is the Laser Power Module Temperature. This is checked like other temperatures. If it is higher/lower than first limits then a warning is issued to cool equipment. If higher/lower than second limit, a non-critical failure is issued, acquisition is halted, and system must be shutdown to cool off.

(7) AFSAmpTemp Checks the actual temperature of the Auto Focus System amplifier in the same manner as other temperatures. This test checks a bit reported from the auto focus system (AFS) amplifier temperature (OEM provided data). If the test resultant bit is 0, then acquisition is halted and user action is required.

Referring again to FIG. 3, after completion of some or all of the ADCs, if any one of the tests resulted in a halting of data acquisition, then process 300 may return to the standby mode of step 301 such that the system can be appropriately serviced, or reconfigured in response to a particular test or check that has failed. Assuming the ADCs have not caused a halting of spectral data acquisition, then process 300 proceeds to step 315 at which an initial set of ten (10) dark spectra is taken. That is, a series of spectra is taken during which there is no corresponding laser pulse. A median value of all of these spectra is then calculated, and this median value is used in subsequent spectral analysis by subtracting away the median value from a given spectral data acquisition, and thereby remove noise and background effects. Those skilled in the art will appreciate that the number of dark spectra taken is an exemplary number and that it may be desirable to include more or fewer initial dark spectral data collections.

Next, at step 320, a "kinetic series" (KS) loop is initialized. A KS is a group of instructions that can be loaded into the ICCD to be performed in series. This functionality is provided by the Andor ICCD used in an actual implementation of the present invention, and permits a more autonomous operation of the ICCD, i.e., an operating mode that does not require constant externally provided instructions. The advantage of this operational method, as opposed to a conventional method in which the ICCD is given instructions prior to each frame it records, is that this KS mode allows the ICCD to acquire frames faster—at 25 per second. This higher data rate results in higher detection probabilities. Of course, it may also be desirable to operate ICCD 220 conventionally.

Once ICCD 220 is ready, laser 210 is pulsed and a Raman spectrum is acquired, at step 325, using the spectrograph 222 and ICCD 220, as is well-known in the art. In accordance with the present invention, the spectral data thus acquired is then subjected to a data quality check (DQC) at step 330 to confirm the usefulness of the data. As detailed below, several tests are conducted on selected system components, as well as on the spectral data itself while it is stored in memory, but before it is allowed to be further processed by a separate agent identification computer (AIC) (not shown) or agent identification routine/algorithm that is performed by processor 130.

Data Quality Checks (DQCs):

The following DQCs are preferably performed in accordance with an embodiment of the present invention.

(1) Linear Focus Actuator (LFA) Fault. This test determines if an autofocus actuator (associated with telescope 232) has faulted, in which case telescope 232 may not be in focus. If this is the case, the data just collected is rejected for further processing.

(2) LFA Brake Engaged. This test determines if the LFA brake is engaged. If it is, then the telescope actuator may be in a safe mode and, as such, the acquired data may be suspect, and, as a consequence, the data is likewise not sent for further processing.

(3) LFA Focus Mode. This test determines if the LFA mode is Auto, FFAuto (fixed focus auto), or Command. Auto means the system is auto focusing. When the system is mounted in a vehicle and the vehicle is moving, the distance to the ground varies (potholes, rocks, vegetation, etc). In Auto mode, the telescope primary is moved to keep the system in focus (within certain limits, of course). FFAuto mode is used when the distance to the ground varies rapidly (e.g. when the system is over tall grass) in which case the focus is fixed at a statistically computed sensor range for a short time (e.g. 1 second). Command mode fixes the telescope focus to a user-commanded range. If it is not any of these correct modes, then telescope 232 may not be focused, and the acquired data is, once again, rejected.

(4) Laser Energy Range. This test determines if the laser energy is within an acceptable range. If it lies outside this range, then reject the current spectrum data. (5) Saturated Spectrum. This test determines if the acquired spectral data is significantly saturated. The signal spectrum is preferably analyzed before the median dark spectrum is subtracted from the collected data. Specifically, a count is made of the number of pixels in the signal spectrum with amplitudes greater than a second pre-determined value. If more than a predetermined number is found, then the spectrum is considered saturated and the spectrum is rejected.

(6) Low Amplitude Spectrum. This test is the complement to the Saturated Spectrum test. Here, it is determined if the spectrum amplitude is too low. First, the median dark spectrum is subtracted from the signal spectrum. A count is then made of the number of pixels in the dark-subtracted spectrum with amplitudes>a pre-determined value. If the number of pixels with amplitudes>greater than this value is less than or equal to a second predetermined value, then the spectrum is rejected. Since low signals result in low signal-to-noise spectra, this test is an example of a signal-to-noise ratio (SNR) test and amounts to rejecting the spectrum if its SNR is too low.

(7) Split (corrupted) Spectrum. This test determines if the acquired spectrum is to be rejected due either to corrupted data from the ICCD or due to unusually high fluorescence values from the surface. This is determined by testing if the amplitude of pixels at the unused edge of the spectrum is higher than a predetermined limit. These pixels are blocked from light by the mounting structure of the ICCD and should have no significant amplitudes. The presence of significant amplitudes in these pixels means that either the spectrum is faulty (pixel amplitudes have been ordered incorrectly due to the spectrum being split during readout and reassembled wrong) or that the light level on the ICCD is so high that light has "leaked" onto the edge pixels and the spectrum is not reliable. This can occur even though the spectrum is not saturated. While a test of the total integrated amplitude under the spectrum could be used as an alternate fluorescence test, such a test would not be able to distinguish corrupt spectra.

With reference again to FIG. 3, at step 330, if one or more tests associated with the DQCs have failed, then it is determined whether, at step 335, failure was a result of saturation or low amplitude. If so, the gain of the ICCD is preferably adjusted (in the appropriate direction) to compensate for the problem. A gain adjustment loop is described later herein with reference to FIG. 4. If, at step 330, all of the DQCs passed, then, at step 340, the collected spectral data is added to a block of spectral data that comprises up to 50 individual Raman spectral data sets associated with laser pulses to be processed together by processor 130 in CAPPS 105 processing the block of spectral data, including, among other things, accessing a library of agent Raman signatures that are stored in memory. As is well-known in the art, by matching the collected spectra with saved patterns it is possible to identify agents such as chemical and biological substances. The block size of 50 disclosed herein is somewhat arbitrary, but in an actual implementation, the number turns out to be a good compromise for digital signal processing in a batch manner. If for any reason a DQC failed, then data associated with the given laser pulse is not added to the block of 50. In other words, poor quality spectral data is precluded from being processed by processor 130, thereby saving time, preventing possible false detections, and making the entire data acquisition process more efficient.

If at step 335, it was determined that the DQCs failed for a reason other than low signal level or saturation, or after step 340 (adding the spectral data for a given laser pulse to the block of 50), process 300 continues to step 345. At this next step it is determined whether a total of 3000 signal spectra (e.g., data records for respective laser pulses) have been stored in memory 115. A block of 3000 signal spectra is a convenient number for a log file that can be stored separately along with its associated DQC and ADC results data. Once again, this particular number is somewhat arbitrary and those skilled in the art will appreciate that any log file size may be implemented, depending, for example, on the nature of the computing equipment and memory available. If there is still room for additional data in the block of 3000 signal spectra, then process 300 loops back to step 325 for a next laser pulse and spectra acquisition.

If it was determined at step 345 that a total of 3000 (or whatever the set number is) signal spectra have been stored, then a log file with the 3000 spectra is separately stored along with its associated DQC and ADC results data, step 347. As shown in FIG. 3, during or immediately after this log file storing step, several, e.g., three, new dark spectra are collected at step 350 and, in an actual implementation of the present invention, the oldest three of the original ten dark spectra are removed and the three newly-collected dark spectra are added in a first in, first out (FIFO) manner. A new median is then calculated and used for background noise cancellation in subsequent non-dark spectral data processing. Also at this time, at step 355, the KS loop previously initialized is closed, and a new set of ADCs is performed, as indicated by step 360. If there is a failure in an ADC warranting shut down or halting of further data acquisition, then process 300 is passed to step 365 and, ostensibly, back to standby mode 301. If the ADCs of step 360 all pass, then process 300 loops back to step 320 to initialize a new KS loop, i.e., to again begin spectral data collection in connection with laser pulses.

In accordance with the present invention, the storing of a log file comprising 3000 signal spectra is a convenient time during process 300 to reaffirm that the overall Raman system 100 is operating properly. In a preferred embodiment, the laser pulses at 25 Hz and, thus, the ADCs of step 360 are performed about every 120 seconds, or two minutes. In the field, this ADC frequency has been deemed suitable to maintain confidence in the spectral data being collected. Of course, it may be desirable to increase or decrease ADC frequency, depending on variables such as ambient weather conditions, age of equipment, and the like. Moreover, it may be desirable to perform ADCs during standby mode (step 301) such that an operator will be alerted to potential problems even before use of the system is initiated.

Referring back to step 335, if a DQC failed due to low signal or saturation, the gain of the ICCD 220 is preferably adjusted in the appropriate direction. This is accomplished via process 400 depicted in FIG. 4. As shown, at step 401, a single scan mode is initialized. This is an Andor-provided ICCD mode, different from a kinetic series (KS) mode, wherein the gain of the ICCD can be adjusted. Alternatively, depending on the type of ICCD, the gain may be adjusted while still in KS mode, such that step 401 can be eliminated. In either case, the current or present gain of the ICCD is modified up or down as the case may be at step 405.

Figure 4:
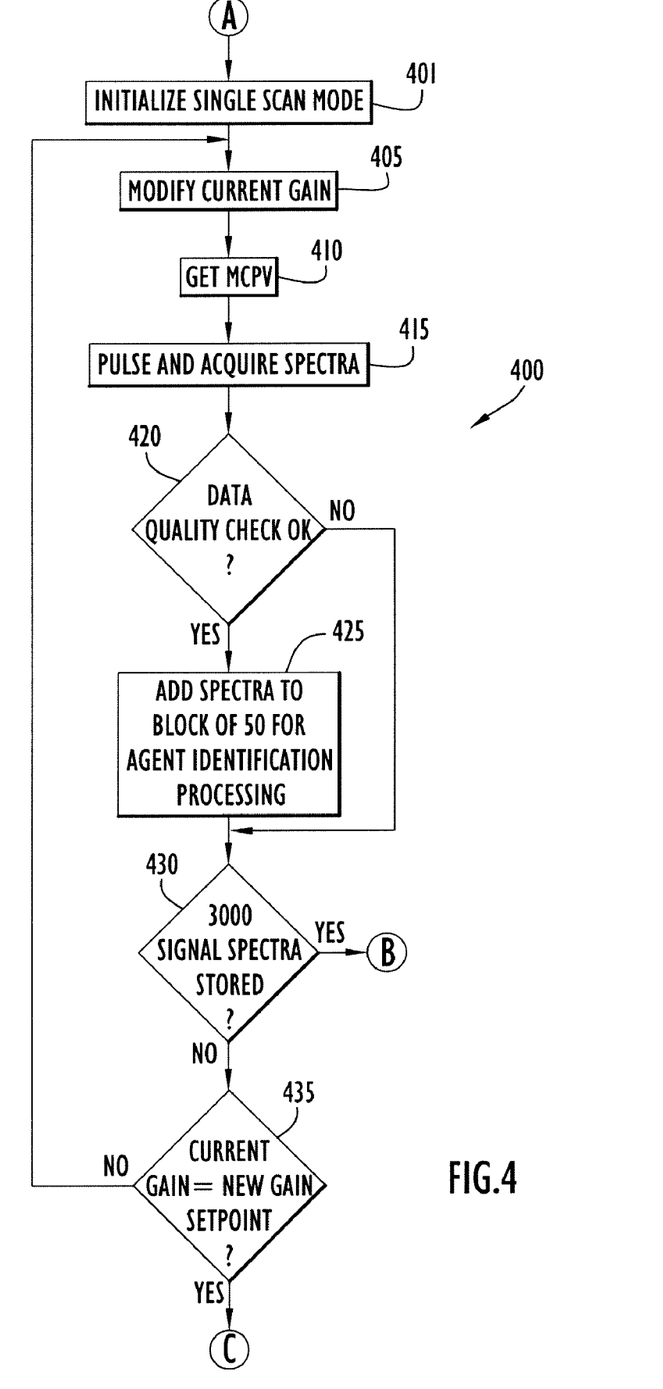

In accordance with an embodiment of the present invention, first a NewGainSetPoint is set by incrementing or decrementing a CurrentGainSetpoint, in view of whether there was low signal or saturation. A value delta gain is then computed as delta gain=NewGainSetpoint−CurrentGainSetting.

Then, if delta gain>5 then current gain setting=current gain setting+5;

If |delta gain|<5 then current gain setting=NewGainSetPoint; or

If delta gain<−5 then current gain setting=current gain setting−5.

Once the current gain setting is established, process 400 moves to step 410 to capture the ICCD's Micro-Channel Plate Voltage (MCVP), which is indicative of the actual current gain of the ICCD. At least with the Andor ICCD used in an actual implementation of the present invention, there is sometimes a time lag between setting a desired ICCD gain, and the ICCD actually operating with that gain value. As such, step 410 is used to capture the actual gain of the ICCD immediately prior to a next pulse of the laser and subsequent collection of a Raman spectrum (step 415). The thus captured value for the ICCD's MCVP is converted to a digital gain value using a simple relation, and this digital value is written to a pulse header, i.e., a header of a data record for the spectral data collected for that laser pulse. Additionally, the AIC may utilize the digital gain value in its processing.

Process 400 then continues with step 420, which tests the quality of the collected spectral data and determines whether it should be stored for further processing. If not, process 400 skips to step 430. If the collected data passes the DQCs, then at step 425, the data is stored in the block of 50 spectra data records, as previously described, for processing by an AIC or corresponding routine or algorithm. Also, as before, it is determined whether this latest spectral data record was the last of 3000 records for a log file and, if so, process 400 passes control back to step 350 in FIG. 3 for dark spectra acquisition and median update. If the current 3000 data record log is not full, then process 400 moves to step 435 wherein it is determined whether the current gain (derived from the reading the ICCD's MCVP) equals the new desired gain set point. If not, process 400 loops back to step 405 where the gain is again adjusted.

If the current gain does equal the desired new gain set point, then process 400 is complete and the methodology continues with step 320 of FIG. 3, where a new kinetic series loop is initialized.

From the foregoing, those skilled in the art will appreciate that embodiments of the present invention described herein provide a systematic approach to ensuring that Raman spectral data (or virtually any optical data) is properly collected and has value. In other words, embodiments of the present invention are designed to reject data that is likely of little value as a result of system operating conditions. Embodiments of the present invention also systematically and regularly monitor several system components in an effort to ensure that collected data does not include inaccuracies attributable to equipment malfunctions, as well as to monitor system trends that may be presented to a user of the system through one more warnings or alerts.

The systems and methods described herein may be embodied in other specific forms without departing from the spirit or essential characteristics thereof. The foregoing embodiments are therefore to be considered in all respects illustrative and not meant to be limiting.

What is claimed is:

1. A method for operating a Raman sensor, comprising:
performing a plurality of ancillary data checks that monitor operating conditions of system components of a Raman sensor comprising a laser, a spectrograph and an intensified charge coupled device (ICCD);

acquiring Raman spectral data as a result of pulsing the laser and passing returning light from a sample illuminated by the laser through the spectrograph and capturing Raman spectra of the spectrograph by the ICCD;

performing a plurality of data quality checks related to the Raman spectral data acquired during said acquiring step;

determining, based on results of the data quality checks, whether to further process the Raman spectral data acquired during said acquiring step and, if so, storing the Raman spectral data acquired during said acquiring step for further processing;

repeating successively, a predetermined number of times, said step of acquiring Raman spectral data and said step of performing a plurality of data quality checks related to the Raman spectral data, and then again performing said step of performing a plurality of ancillary data checks;

storing in a log file a series of acquired Raman spectral data, and closing the log file after said predetermined number of times; and after said closing step, acquiring a predetermined number of dark spectral data and revising a previously calculated dark spectral data median.

2. The method of claim 1, wherein said step of performing a plurality of ancillary data checks comprises monitoring a state of each of the ICCD and the laser.

3. The method of claim 2, further comprising monitoring a temperature of one or more components of the Raman sensor.

4. The method of 1, wherein said step of performing a plurality of ancillary data checks comprises monitoring a linear focus actuator of an autofocus subsystem to maintain proper focus of the optics which collect the Raman spectrum.

5. The method of claim 1, wherein said step of performing a plurality of data quality checks comprises monitoring laser energy.

6. The method of claim 1, wherein said step of performing a plurality of data quality checks comprises determining whether the Raman spectral data acquired during said acquiring step is saturated or is of insufficient amplitude.

7. The method of claim 1, further comprising halting further Raman spectral data acquisition upon a failure of one of the plurality of ancillary data checks.

8. The method of claim 1, further comprising adjusting a gain for the ICCD in response to one of the plurality of data quality checks.

9. A method of operating a Raman spectroscopy device, the device comprising a laser, a spectrograph, an intensified charge coupled device (ICCD), and an autofocus subsystem, the method comprising:

performing a plurality of ancillary data checks that monitor operating conditions of at least the laser, the ICCD, and the autofocus subsystem;

acquiring Raman spectral data by pulsing the laser and collecting resulting Raman spectra with the ICCD via the spectrograph;

performing a plurality of data quality checks related to the Raman spectral data acquired during said acquiring step;

determining, based on results of the data quality checks, whether to further process the Raman spectral data acquired during said acquiring step and, if so, storing the Raman spectral data acquired during said acquiring step for further processing;

repeating successively, a predetermined number of times, said step of acquiring Raman spectral data and said step of performing a plurality of data quality checks related to the Raman spectral data;

storing in a log file a series of acquired Raman spectral data, and closing the log file after said predetermined number of times; and after said closing step, acquiring a predetermined number of dark spectral data and revising a previously calculated dark spectral data median.

10. The method of claim 9, further comprising, repeating said step of performing a plurality of ancillary data checks after said repeating successively.

11. The method of claim 9, further comprising halting further Raman spectral data acquisition if one of the plurality of ancillary data checks indicates a failure.

12. The method of claim 9, further comprising storing Raman spectral data that has passed the plurality of data quality checks for agent identification processing.

13. The method of claim 9, further comprising adjusting a gain of the ICCD in response to at least one of the plurality of data quality checks.

14. A Raman spectroscopy system, comprising:

a laser that is configured to pulse at a predetermined frequency;

an autofocus subsystem that controls focus of a telescope that is directed, optically, at the same spot illuminated by the laser;

a spectrograph and an intensified charge coupled device (ICCD) that are configured to receive Raman spectra resulting from the laser pulse via the telescope; and a processor and associated memory, the memory being configured to store the individual Raman spectra as individual records of Raman spectral data as captured by the ICCD, the processor being configured to execute a plurality of ancillary data checks that monitor operating conditions of at least the laser, the ICCD, and the autofocus subsystem, and to execute a plurality of data quality checks related to the usefulness of the Raman spectral data, wherein the processor is further configured to determine, based on results of the data quality checks, whether to store Raman spectral data in a log file for further processing and whether to repeat execution of the plurality of ancillary data checks, and wherein the processor is still further configured to store in the log file a series of acquired Raman spectral data, to close the log file after a predetermined number of series have been stored; and after the log is closed to acquire a predetermined number of dark spectral data and revise a previously calculated dark spectral data median.

15. The system of claim 14, further comprising a rangefinder subsystem that operates in conjunction with the autofocus subsystem.

16. The system of claim 14, wherein the processor is configured to determine whether a given collected Raman spectrum is saturated, corrupted, or is of insufficient amplitude.

17. The system of claim 16, wherein the processor is configured to initiate a routine to adjust a gain of the ICCD when a determination is made that the given collected Raman spectrum is saturated or is of insufficient amplitude.

* * * * *

UNITED STATES PATENT AND TRADEMARK OFFICE
CERTIFICATE OF CORRECTION

PATENT NO. : 8,306,780 B2
APPLICATION NO. : 12/359589
DATED : November 6, 2012
INVENTOR(S) : Thomas H. Chyba It is certified that error appears in the above-identified patent and that said Letters Patent is hereby corrected as shown below:

On the Front Page of the Patent, in the "Other Publications" section, replace "Carter et al., "Standoff Detection of High Explosive Materials at 50 Meters in Ambient Light Conditions Using a Small Raman Instrument", vol. 59, No. 6, Mar. 17, 2005, pp. 769-775." with -- Carter, et al., "Standoff Detection of High Explosive Materials at 50 Meters in Ambient Light Conditions Using a Small Raman Instrument", Appl. Spectrosc. Vol. 59, No. 6, Mar. 17, 2005, pp. 769-775. --; and Column 10, line 64, replace "comprise for digital" with -- compromise for digital --.

Signed and Sealed this
Fifth Day of March, 2013

Teresa Stanek Rea
*Acting Director of the United States Patent and Trademark Office*